US00PP12612P2

(12) United States Plant Patent
Woods

(10) Patent No.: US PP12,612 P2
(45) Date of Patent: May 7, 2002

(54) HIBISCUS PLANT NAMED 'NOTWOODTWO'

(75) Inventor: Roderick Ian Woods, Great Shelford (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 09/566,448

(22) Filed: May 8, 2000

(51) Int. Cl.[7] ..... A01H 5/00
(52) U.S. Cl. ..... Plt./257
(58) Field of Search ..... Plt./257

(56) References Cited

PUBLICATIONS

UPOV–ROM GTITM Computer Database 2001/01, Feb. 6, 2001, GTI Jouve Retrieval Software, Citation for 'Notwoodtwo'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Hibiscus plant named 'Notwoodtwo', characterized by its upright plant habit; very freely branching habit; dense and bushy appearance; and attractive and numerous pure white-colored flowers that are large and semi-double with numerous stamenoid petaloids.

1 Drawing Sheet

BACKGROUND OF THE INVENTION

The present Invention relates to a new and distinct cultivar of Hibiscus plant, botanically known as *Hibiscus syriacus*, and hereinafter referred to by the cultivar name Notwoodtwo.

The new Hibiscus is a product of a breeding program conducted by the Inventor in Great Shelford, United Kingdom. The objective of the breeding program was to create new Hibiscus cultivars with new and unique flower colors and types.

The new Hibiscus originated from open-pollinations of various unidentified seedling selections of *Hibiscus syriacus*. The new Hibiscus was discovered and selected by the Inventor as a flowering plant within the progeny from these crosses in a controlled environment in Great Shelford, United Kingdom. The new Hibiscus was selected on the basis of its flower color and type.

Asexual reproduction of the new cultivar by cuttings taken at Woodbridge, United Kingdom, since 1988 has shown that the unique features of this new Hibiscus are stable and reproduced true to type in successive generations.

SUMMARY OF THE INVENTION

Plants of the cultivar Notwoodtwo have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Notwoodtwo'. These characteristics in combination distinguish 'Notwoodtwo' as a new and distinct cultivar:

1. Upright plant habit.

2. When pinched, very freely branching habit; dense and bushy appearance.

3. Attractive and numerous pure white-colored flowers that are large and semi-double with numerous staminate petaloids.

Plants of the new Hibiscus differ from other cultivars of Hibiscus known to the Inventor in its unique combination of flower form and petal coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which more accurately describe the actual colors of the new Hibiscus.

The photograph at the top of the sheet comprises a side perspective view of a typical plant of 'Notwoodtwo'.

The photograph at the bottom of the sheet comprises a close-up view of a typical flower of 'Notwoodtwo'.

DETAILED BOTANICAL DESCRIPTION

In the following description, color references are made to The Royal Horticultural Society Colour Chart except where general terms of ordinary dictionary significance are used. Plants were grown in Grand Haven, Mich. under full sun field conditions which closely approximate commercial production conditions. Day temperatures ranged from 10 to 32° C. and night temperatures ranged from 4 to 24° C. Plants used for the description and photographs were about four years old and grown in the ground.

Botanical classification: *Hibiscus syriacus* cultivar Notwoodtwo.

Parentage: Open-pollination of various unidentified seedling selections of *Hibiscus syriacus*, not patented.

Propagation:

*Type cutting.*—By softwood cuttings.

*Time to initiate roots.*—Summer: About 21 days at 32° C. Winter: About 28 days at 20° C.

*Time to produce a rooted cutting or liner.*—Summer: About 56 days at 32° C. Winter: About 70 days at 20° C.

*Root description.*—Thick and fleshy.

Plant description:

*Crop time.*—From cuttings, about one growing season is required to produce a flowering finished plant in a one-gallon container.

*Form.*—Mostly upright; inverted triangle; dense and bushy perennial.

*Usage.*—Appropriate for one to three-gallon containers.

*Plant height, soil level to top of plant plane.*—About 2.7 m.

*Plant width.*—About 1.75 m.

*Vigor.*—Moderate to rapid growth rate.

*Branching habit.*—When pinched, very freely branching with about 106 lateral branches per plant.

*Lateral branches.*—Length: About 69 cm. Diameter: About 4.5 mm. Internode length: About 6 cm. Texture: Smooth; glabrous. Color: Young, 137A; woody, 198A.

*Foliage description.*—Leaves simple, generally symmetrical and long persisting. Tolerant to stresses. Arrangement: Typically alternate, but occasionally whorled with multiple leaves per node. Quantity per lateral branch: Typically about 42. Length: About 4.5 cm. Width: About 3 cm. Shape: Rhomboid to ovate, three-lobed. Apex: Acute. Base: Broadly cuneate to rounded. Margin: Coarsely dentate. Texture, both surfaces: Glabrous; medium thickness. Venation: Pinnate. Color: Young foliage, upper surface: 143B. Young foliage, lower surface: 143B. Mature foliage, upper surface: 146A; venation, 146A. Mature foliage, lower surface: 146B; venation, 146B. Petiole: Length: About 0.9 mm. Diameter: About 2.5 mm. Texture: Pubescent. Color: 146A.

Flower description:

*Flower type and habit.*—Semi-double rounded flowers arising from leaf axils. Freely flowering. Flowers last about one day on the plant. Not persistent. Not fragrant.

*Natural flowering season.*—Continuously flowering from mid-summer through fall.

*Quantity of flowers.*—About 11 per lateral branch; more than 1,100 per plant.

*Flower diameter.*—About 10.5 cm.

*Flower depth* (*height*).—About 2.5 cm.

*Flower buds* (*just showing color*).—Length: About 3.5 cm.

*Diameter.*—About 1.5 cm. Shape: Ovate. Rate of opening: About one day. Color: 145B.

*Petals.*—Arrangement/appearance: Single whorl of five petals. Length: About 5 cm. Width: About 5 cm. Shape: Obovate. Apex: Rounded. Margin: Entire; undulate. Texture: Smooth. Color: Upper surface, when opening: More white than 155D. Lower surface, when opening: More white than 155D. Upper surface, opened flower: More white than 155D, becoming 155B with subsequent development. Lower surface, opened flower: More white than 155D. Petaloids: Variable shape and size. Quantity: About 15 to 48. Arrangement: Whorled. Length: About 1 to 3.5 cm. Width: About 0.25 to 1.5 cm. Shape: Mostly spatulate; margin, entire and undulate. Texture, both surfaces: Glabrous. Color, immature and mature: More white than 155D.

*Calyx.*—Arrangement: Star-shaped, sepals, five, fused. Sepal length: About 1.7 cm. Sepal width: About 7 mm. Sepal shape: Acute. Sepal apex: Acute. Sepal margin: Entire. Color, both surfaces: 147A.

*Peduncle.*—Length: About 1.2 cm. Strength: Moderately strong. Color: 138A.

*Reproductive organs.*—Stamens: Quantity: About 10 per flower. Anther length: About 1.5 mm. Anther color: 155B. Pollen amount: Moderate. Pollen color: 155B. Pistils: Pistil quantity per flower: One. Pistil length: About 3 cm. Stigma shape: Five-parted; rounded. Stigma color: White, close to 155B. Style length: About 3 cm. Style color: White, close to 155B.

*Fruit.*—Type: Capsule. Length: About 1.2 cm. Diameter: About 8 mm. Shape: Ovate. Texture: Rugose. Color: 155A.

*Seed.*—Length: About 2 mm. Diameter: About 1 mm. Texture: Glabrous.

Disease insect resistance: Under commercial production conditions, plants of the new Hibiscus have not been noted to be resistant to pathogens and insects common to Hibiscus.

Cold hardiness: Plants of the new Hibiscus have been observed to be tolerant to temperatures as low as −32° C.

It is claimed:

1. A new and distinct cultivar of Hibiscus plant named 'Notwoodtwo', as illustrated and described.

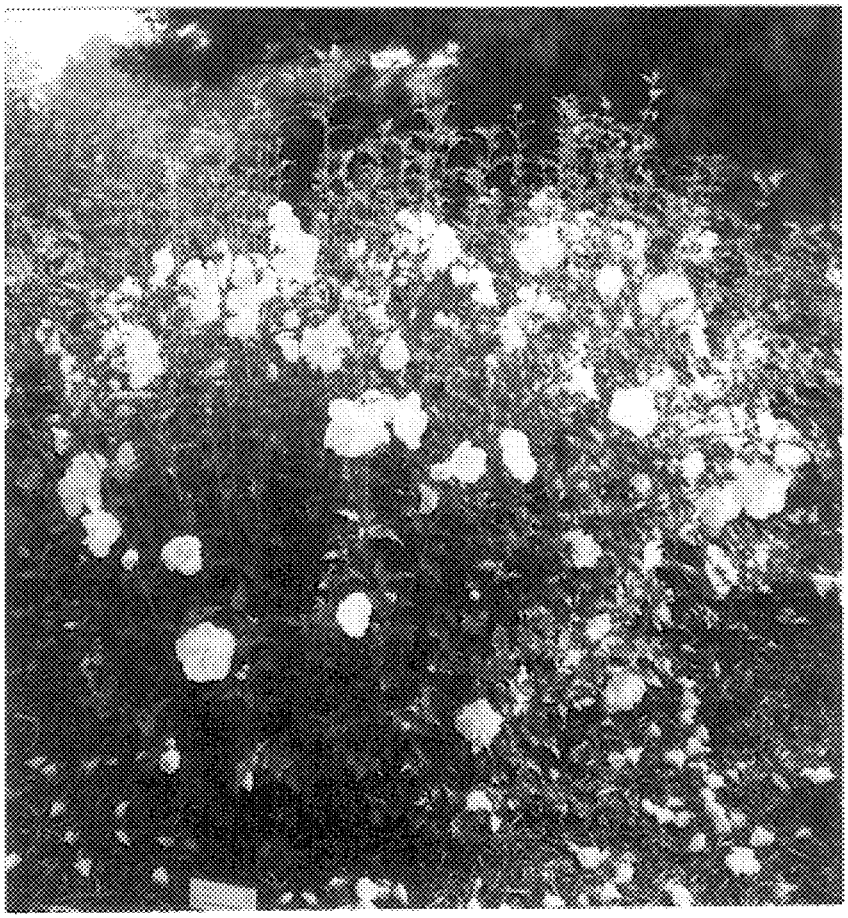
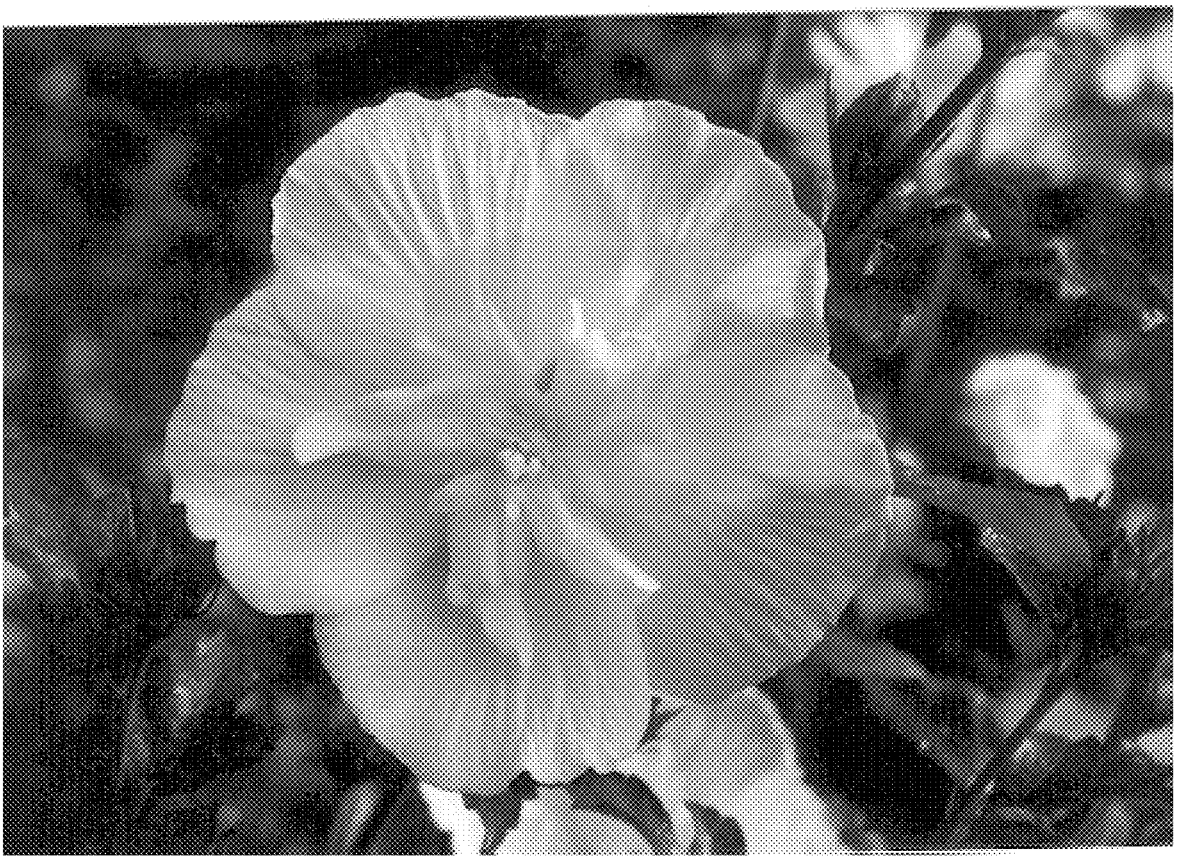

* * * * *